United States Patent [19]

Arkans

[11] 4,328,814
[45] May 11, 1982

[54] PRECORDIAL ECG STRIP

[75] Inventor: Edward J. Arkans, Schaumburg, Ill.

[73] Assignee: The Kendall Company, Boston, Mass.

[21] Appl. No.: 156,245

[22] Filed: Jun. 4, 1980

[51] Int. Cl.³ .................................................. A61B 5/04
[52] U.S. Cl. ......................................... 128/640; 128/641
[58] Field of Search ..................... 128/639–641, 128/644, 798, 802, 803

[56] References Cited

U.S. PATENT DOCUMENTS

| | | | |
|---|---|---|---|
| 2,943,628 | 7/1960 | Howell | 128/640 |
| 3,380,445 | 4/1968 | Frasier | 128/639 |
| 3,572,322 | 3/1971 | Wade | 128/640 |
| 3,587,565 | 6/1971 | Tatoian | 128/640 |
| 3,888,240 | 6/1975 | Reinhold, Jr. et al. | 128/644 |
| 4,072,145 | 2/1978 | Silva | 128/644 |
| 4,082,086 | 4/1978 | Page et al. | 128/640 |
| 4,082,087 | 4/1978 | Howson | 128/640 |
| 4,250,878 | 2/1981 | Jacobsen et al. | 128/803 X |

*Primary Examiner*—Lee S. Cohen
*Attorney, Agent, or Firm*—Powell L. Sprunger

[57] ABSTRACT

A precordial ECG strip comprising, a plurality of electrode assemblies with each comprising a housing having a front surface, a recess received in the front surface of the housing, an ECG electrode received in an inner part of the recess, and a conductive lead having one end electrically connected to the electrode. The electrode assemblies are connected together in a row with the leads of the electrode assemblies extending along the row of the electrode assemblies.

3 Claims, 3 Drawing Figures

PRECORDIAL ECG STRIP

BACKGROUND OF THE INVENTION

The present invention relates to ECG electrodes.

Before the present invention, ECG electrodes have been utilized to monitor the electrical activity of the heart by suitable equipment, such as a recorder. During certain procedures, an electrode is positioned on a patient's chest, and is connected to a recorder which automatically selects leads. However, the automatic feature of the recorder cannot be utilized with a single electrode since the electrode must be moved about to various locations. On the contrary, if a plurality of electrodes are used, the placement of the separate electrodes and connection of the respective leads to the recorder has proved to be inconvenient and time-consuming to the hospital personnel.

SUMMARY OF THE INVENTION

A feature of the present invention is the provision of a precordial ECG strip.

The strip of the present invention comprises, a plurality of electrode assemblies with each comprising a housing having a front surface, a recess received in the front surface of the housing, an ECG electrode received in an inner part of the recess, and a conductive lead having one end electrically connected to the electrode. The strip has means flexibly connecting the electrode assemblies together in a row with the leads of the electrode assemblies extending along the row of electrode assemblies.

A feature of the present invention is that the connected electrode assemblies facilitate attachment of the strip to the proper position on a patient's chest.

Another feature of the invention is that the other ends of the leads may be attached to a connector.

Thus, a feature of the present invention is that the strip facilitates connection of the leads to ECG monitoring equipment, such as a recorder.

Yet another feature of the invention is that an automatic feature of the recorder which selects leads may be utilized with the strip of the present invention.

Further features will become more fully apparent in the following description of the embodiments of this invention and from the appended claims.

DESCRIPTION OF THE PREFERRED EMBODIMENTS

Figure 1:
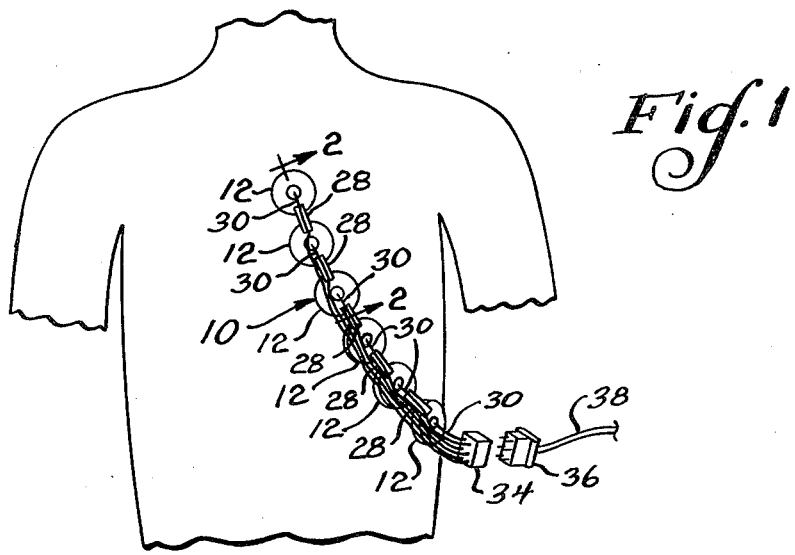
FIG. 1 is a perspective view of a precordial ECG strip of the present invention as attached to a patient.
Figure 2:
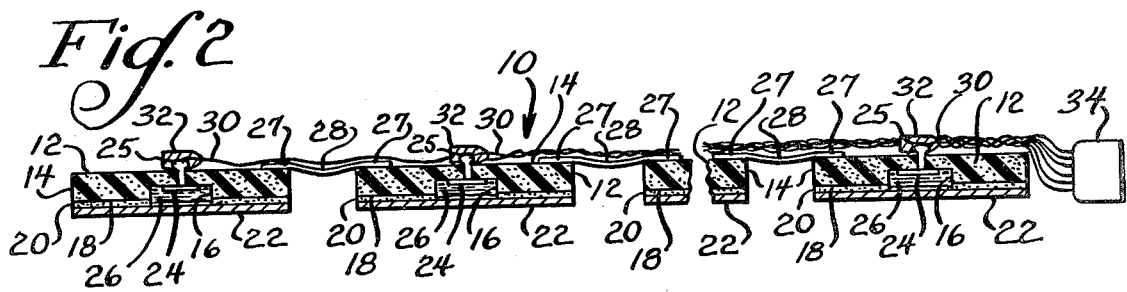
FIG. 2 is a fragmentary sectional view taken substantially as indicated along the line 2—2 of FIG. 1.
Figure 3:
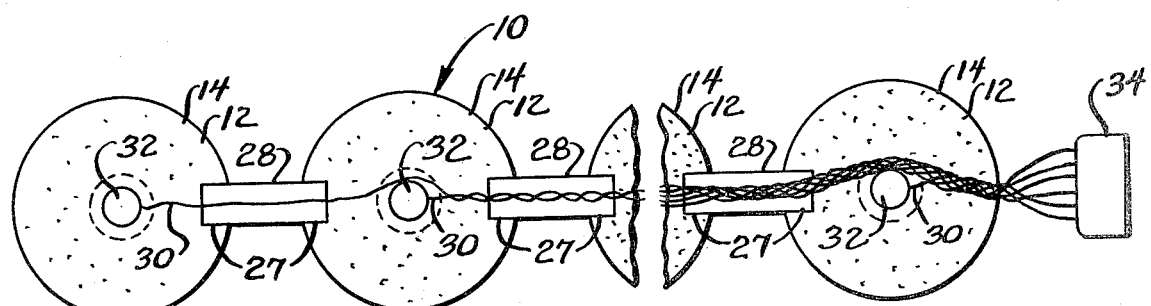
FIG. 3 is a fragmentary upper plan view of the strip of FIG. 1.

Referring now to FIGS. 1-3, there is shown a precordial ECG strip generally designated 10 comprising a plurality of electrode assemblies 12, with the strip 10 preferably having six electrode assemblies 12 in the strip, as shown. Each of the electrode assemblies 12 has a housing 14 comprising a foam pad with a central recess 16 in a front surface 18 of the housing 14. The housings 14 have adhesive 20 on the front surface 18 of the housing 14, and a release sheet 22 releasably covering the adhesive 20. Each of the electrode assemblies 12 has a conductive ECG electrode 24 received in an inner part of the recess 16, with the electrode 24 having a post 25 extending through the back side of the housing 14. The recess 16 of each electrode assembly 12 is filled with a conductive gel 26 exending from the electrode 20 to the front surface 18 of the housing 14.

The strip 10 has a plurality of strips 28 of flexible material having opposed ends 27 connected to adjacent housing pads. As shown, the strips 28 are attached to the pads in a manner to place the electrode assemblies 12 in the configuration of an elongated row, with the strips 28 retaining the adjacent pads in the row configuration and permitting movement of the adjacent pads relative to each other. The strips 28 may be made of a suitable material such as metallic foil or paper.

Each of the electrode assemblies 12 has a conductive lead 30 having one end attached to a suitable connector 32. The connectors 32 may be releasably attached to the posts 25 of the electrodes 24 with the one end of the leads 30 electrically connected to the electrodes 24. As shown, the leads from the electrode assemblies 12 extend along the row of electrode assemblies 12, and the other ends of the leads are attached to a connector 34. As shown in FIG. 1, the strip connector 34 may be releasably attached to a connector 36 of electrical monitoring equipment, such as a recorder, with a cable 38 of the electrical equipment being electrically connected through the connectors 36 and 34 to the leads 30 of the electrode assemblies 12.

In use, the release sheets 22 are removed from the electrode assemblies 12 in order to expose the adhesive 20 on the housings 14, and permit attachment of the electrode assemblies 12 to the chest of a patient while the flexible strips 28 permit adjustment of the position of the electrode assemblies 12 relative to each other during attachment. In a preferred form, the leads 30 are preattached to the various electrode assemblies 12, and the connector 36 of the electrical monitoring equipment may be readily attached to the connector 34 of the strip 10 in order to establish electrical connection between the electrical equipment and the electrodes 24 of the electrode assemblies 12.

Thus, in accordance with the present invention, the electrode assemblies 12 may be attached to the patient in a convenient and simplified manner. In addition, the leads 30 of the electrode assemblies 12 may be connected to suitable electrical monitoring equipment in a simplified manner through use of one connector 34 for the electrode assemblies 12. The strip 10 of the present invention may be utilized in connection with recording equipment which has an automatic selecting feature for the leads 30.

The foregoing detailed description is given for clearness of understanding only, and no unnecessary limitations should be understood therefrom, as modifications will be obvious to those skilled in the art.

I claim:
1. An ECG strip, comprising:
 six electrode assemblies, each electrode assembly comprising a circular one-piece foam pad housing with an upper surface and a flat, uniplanar base or skin contacting surface, means defining a cylindrical recess centrally within but only partially through said foam pad, said recess opening onto said skin contacting surface, a conductive gel filling said recess, and an electrode at the upper end of said recess, and having a portion extending up- wardly through and protruding from said foam pad upper surface;

means flexibly interconnecting said six electrode assemblies together in a row comprising five separate individual, relatively thin strips of flexible material having a width substantially less than the width of each housing, each strip interconnecting adjacent electrode assemblies together; and a bundle of six conductive leads extending along the six electrode assemblies in a row and having respective first ends releasably connected to the six electrode assembly protruding electrode portions, respectively, and having second ends attached to a plug connector adjacent one end of the ECG strip.

2. The strip of claim 1 wherein the housings have adhesive on the skin contacting surfaces thereof.

3. The strip of claim 2 including release sheets releasably covering the adhesive on the electrode assemblies.

* * * * *